United States Patent [19]

Yonesaki et al.

[11] Patent Number: 5,056,318
[45] Date of Patent: Oct. 15, 1991

[54] REFRIGERATING AND/OR HEATING DEVICE OF CONTACT TYPE

[75] Inventors: Takahiro Yonesaki, Moriguchi; Akio Furukawa, Osaka; Shin Fujitani, Hirakata; Kenji Nasako, Hirakata; Ikuo Yonezu, Hirakata, all of Japan

[73] Assignee: Sanyo Electric Co., Ltd., Moriguchi, Japan

[21] Appl. No.: 486,469

[22] Filed: Feb. 28, 1990

[30] Foreign Application Priority Data

Mar. 1, 1989 [JP] Japan ................................ 1-50496
Sep. 26, 1989 [JP] Japan ................................ 1-250267

[51] Int. Cl.$^5$ ................................................. F17C 3/10
[52] U.S. Cl. ............................................ 62/48.3; 62/46.2; 62/293
[58] Field of Search .................... 62/46.2, 48.3, 259.3; 165/104.12, 293, 294

[56] References Cited

U.S. PATENT DOCUMENTS

| | | | |
|---|---|---|---|
| 3,929,136 | 12/1975 | Kreeb et al. | 128/303 |
| 3,971,229 | 7/1976 | Privas | 63/3 |
| 4,040,410 | 8/1977 | Libowitz | 126/270 |
| 4,161,211 | 7/1979 | Duffy et al. | 62/46.2 |
| 4,457,136 | 7/1984 | Nishizaki et al. | 62/46.2 |

FOREIGN PATENT DOCUMENTS

| | | |
|---|---|---|
| 0041244 | 12/1981 | European Pat. Off. |
| 0053737 | 6/1982 | European Pat. Off. |
| 0061191 | 9/1982 | European Pat. Off. |
| 3724589 | 1/1988 | Fed. Rep. of Germany |
| 62-158963 | 7/1987 | Japan |
| 1247301 | 9/1971 | United Kingdom |
| 1402632 | 8/1975 | United Kingdom |

*Primary Examiner*—Albert J. Makay
*Assistant Examiner*—John Sollecito
*Attorney, Agent, or Firm*—Armstrong, Nikaido, Marmelstein, Kubovcik & Murray

[57] ABSTRACT

A refrigerating and/or heating device of the contact type utilizing the endothermic and exothermic reactions of a hydrogen absorbing alloy comprises a contact member (16) in the form of a closed container (18) having a contact surface (17) and packed with a hydrogen absorbing alloy (19), a handle member (21) in the form of a closed container (22) packed with another hydrogen absorbing alloy (23), and a gas pipe (25) interconnecting the two members and having a valve (26).

2 Claims, 8 Drawing Sheets

REFRIGERATING AND/OR HEATING DEVICE OF CONTACT TYPE

FIELD OF INDUSTRIAL APPLICATION

The present invention relates to refrigerating and/or heating devices of the contact type adapted to refrigerate or heat the human body or articles through contact therewith utilizing the endothermic reaction or exothermic reaction of hydrogen absorbing alloys.

BACKGROUND OF THE INVENTION

Hydrogen absorbing alloys make endothermic reaction when desorbing hydrogen and make exothermic reaction when absorbing hydrogen. Some of these alloys refrigerate to a low temperature of up to $-20°$ C. as the result of heat absorption.

Unexamined Japanese Patent Publication SHO 62-158963 discloses a refrigerator utilizing the endothermic reaction. This refrigerator comprises two closed containers respectively accommodating two kinds of hydrogen absorbing alloys ($LaNi_5$ and $CaNi_5$) which are different in hydrogen desorption pressure. Hydrogen is desorbed from one of the alloys and absorbed by the other alloy for the hydrogen desorbing alloy to cause endothermic reaction, thereby causing the container containing this alloy to refrigerate the atmosphere over the entire surface thereof.

Thus, the conventional refrigerator is merely adapted to refrigerate the atmosphere by the entire surface of the closed container but is unable to locally refrigerate or heat an article or the human body through contact therewith.

SUMMARY OF THE INVENTION

The main object of the present invention is to provide a device which is portable and easy to operate and which is nevertheless adapted to locally heat or refrigerate the human body or articles by contact therewith.

The present invention provides a device comprising a closed container having a hydrogen absorbing alloy accommodated therein and provided with a contact surface and a valve, the valve being operable to cause the alloy to desorb hydrogen at a suitable time for the contact surface to absorb heat.

The present invention provides another device which comprises a contact member in the form of a closed container having a contact surface and accommodating a hydrogen absorbing alloy, a handle member in the form of a closed container accommodating another hydrogen absorbing alloy, and a valve interconnecting the contact member and the handle member. The contact member is brought into contact with an article with the handle member hold by the hand, and the valve is manipulated to cause the alloy in the contact member to absorb or desorb hydrogen, thereby allowing the contact surface to perform a heat absorbing or evolving action.

Further according to the present invention, the handle member of the above device is provided with a heat conducting surface for effecting the absorption or desorption of hydrogen reversibly.

BRIEF DESCRIPTION OF THE DRAWINGS

FIGS. 4 (A), (B) and (C) are diagrams illustrating how to transport an article with use of a device of the invention;

DETAILED DESCRIPTION OF THE INVENTION

Figure 1:
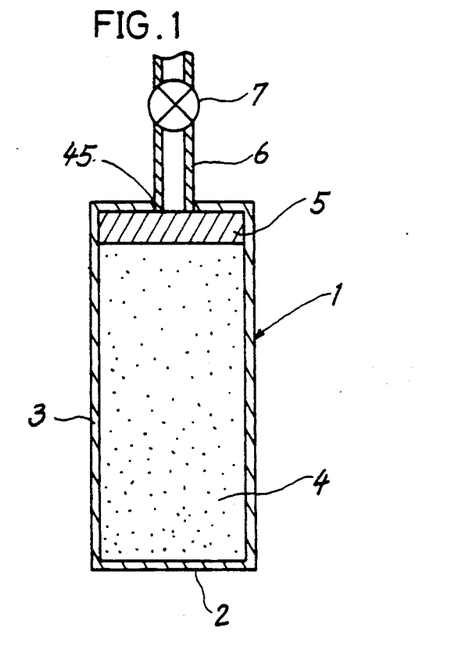
FIG. 1 is a sectional view of a first embodiment of the invention.

FIG. 1 shows a first embodiment as a heat absorbing system wherein a contact member 1 is refrigerated by a valve operation.

With reference to the drawing, the contact member 1 is in the form of a closed container 3 (⅜ inches in diameter, 7 cm in length and 4 $cm^3$ in capacity) having a contact surface 2 at its forward end and containing, for example, 15 g of a finely divided Mm -Ni type hydrogen absorbing alloy (La—Nd—Nialloy) 4. The container 3 is formed in its base end with an opening 45 which is closed with a spillage preventing filter 5 made of a sintered metal or metal netting, not permitting the passage of the alloy but permitting the passage of hydrogen gas only. The interior of the contact member 1 communicates through the filter 5 with a hydrogen discharge pipe 6, which in turn communicates with the atmosphere via a valve 7.

The alloy 4 within the contact member 1 has hydrogen absorbed therein under an increased pressure (about 5 atm.). When the valve 7 is opened with the contact surface 2 held in contact with the human body or an article, the alloy 4 in the contact member 1 under the increased pressure desorbs the hydrogen, which is released to the atmosphere through the discharge pipe 6. Consequently, the alloy absorbs heat from the neighborhood, thereby locally refrigerating the portion in contact with the contact surface 2.

The amount of hydrogen released from the contact member 1 is about 2 liters, and the quantity of heat absorbed by the 15 g of hydrogen absorbing alloy 4 is 6.5 kcal. per mole of hydrogen. Upon the opening of the valve 7, the hydrogen is released instantaneously at a rate of about 10 liters/min and is thereafter released at a very low rate. Almost no hydrogen is discharged in about 7 minutes.

The contact surface 2 further freezes the water in the ambient atmosphere, exerting an adhering force on the site of contact.

Although a usual shutoff valve may be used as the valve 7, the present device is made serviceable as a simplified medical refrigerator for rapidly cooling a local site when the valve used is of such type that it can be readily opened when fractured with fingers.

Figure 1A:
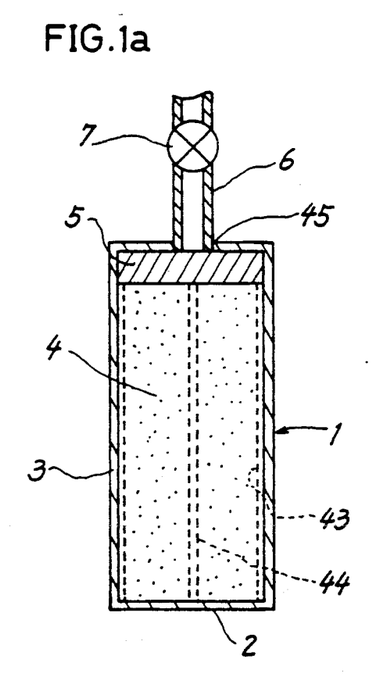
FIGS. 1a and 1b are sectional views showing modifications of the first embodiment.

FIG. 1a shows a modification of the first embodiment wherein the closed container 3 providing the contact member 1 has its side wall covered with an insulating material 43 from inside or outside to diminish heat conduction through the container side wall and cause the contact end surface 2 only to concentrically act for refrigeration. The closed container further has a gas passing linear member 44 of fibrous or porous material extending inside thereof from the filter 5 to the vicinity of the contact surface 2.

When the valve 7 is opened, the hydrogen gas desorbed from the hydrogen absorbing alloy around the linear member 44 flows through the member 44 and rapidly reaches the filter 5, so that the contact member 1 refrigerates uniformly at approximately the same velocity over the entire length thereof. When required, the gas passing linear member 44 may be so treated that although permeable to the gas in the vicinity of the contact surface 2, the surface of the member 44 is impermeable to the gas in the vicinity of the filter 5. This ensures promoted desorption of hydrogen from the alloy in the vicinity of the contact surface, permitting the contact surface 2 to undergo a temperature reduction more concentrically.

Figure 1B:
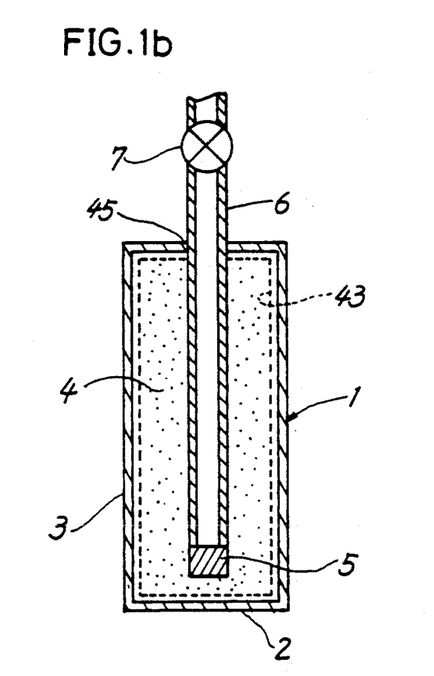

FIG. 1b shows another improvement of the first embodiment. The discharge pipe 6 extends into the closed container 3 and has an open end in the vicinity of the contact surface 2 and a filter 5 closing the open end of the discharge pipe 6.

The heat insulating material 43 covers the entire inside or outside surface of the contact member 2 except the contact surface 2. Since the heat absorption due to the desorption of hydrogen gas from the alloy takes place most effectively in the vicinity of the open end of the discharge pipe 6, the construction of FIG. 1b enables the contact surface 2 to exhibit an enhanced refrigerating action.

Figure 2:
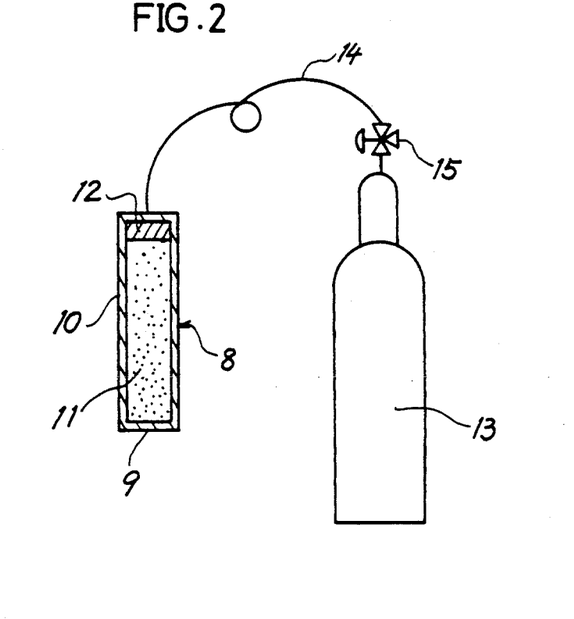
FIG. 2 is a sectional view of a second embodiment.

FIG. 2 shows a second embodiment as a heat evolving system wherein a contact member 8 becomes heated by a valve operation. With reference to this drawing, the contact member 8, which evolves heat, has the same construction as the contact member 1 of the first embodiment. The contact member 8 is in the form of a closed container 10 having a contact surface 9 at its forward end, containing a hydrogen absorbing alloy 11 and is sealed off with a spillage preventing filter 12. The contact member 8 communicates with a high-pressure hydrogen cylinder 13 through the filter 12, a pipe 14 and a valve 15.

The alloy 11 within the contact member 8 is held in a hydrogen-desorbed state under atmospheric or negative pressure. When the valve 15 is opened with the contact surface 9 in contact with an article, the cylinder 13 releases 2 liters of hydrogen into the contact member 8, causing the alloy 11 to absorb the hydrogen Consequently, the alloy 11 evolves heat, heating the contact member 8 to a surface temperature of 70° to 100° C.

When the heat evolving contact member 8 is modified as shown in FIG. 1a or 1b, the temperature of the contact surface 9 can be raised concentrically locally.

The contact member 8 of the second embodiment, as used, has a large quantity of hydrogen gas absorbed by the alloy 11 at a high pressure and can be used as the contact member 1 of the first embodiment.

Figure 3:
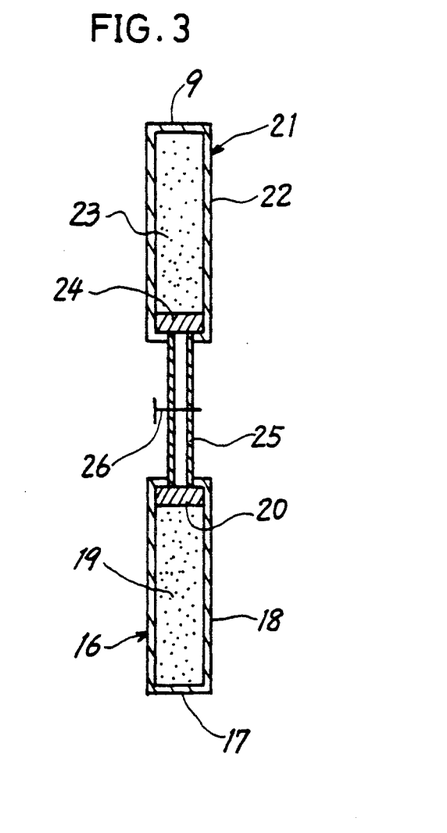
FIG. 3 is a sectional view of a third embodiment.

Further the contact member 1 of the first embodiment as used is at a low pressure, with the hydrogen gas desorbed from the alloy 4, and can therefore be used as the contact member 8 of the second embodiment FIG. 3 shows a third embodiment of the invention which comprises a contact member 16 and a handle member 21 connected thereto.

The contact member 16 is in the form of a closed container 18 having a contact surface 17 at its forward end, containing 15 g of a hydrogen absorbing alloy 19 (La—Nd—Ni alloy) and sealed with a spillage preventing filter 20.

The handle member 21 is in the form of a closed container 22, containing 15 g of another hydrogen absorbing alloy 23 (Zr—Mn alloy) and sealed with a spillage preventing filter 24.

It is desired that the hydrogen absorbing alloys 19, 23 in the contact member 16 and the handle member 21 be different in kind so as to give a great equilibrium pressure difference.

The contact member 16 and the handle member 21 are interconnected by a gas pipe 25 having a valve 26 and communicate with each other through the respective filters 20, 24 and the valve 26.

By varying the internal pressure and temperature of the respective closed containers of the contact member 16 and the handle member 21 and suitably determining the hydrogen desorption pressure, the hydrogen gas can be transferred from one of the containers to the other container as desired reversibly.

Suppose the device is in an initial state in which the alloy 19 of the contact member 16 has hydrogen absorbed therein in advance, with hydrogen desorbed from the alloy 23 of the handle member 21 When the valve 26 is opened with the contact surface 17 of the contact member 16 in contact with an external article, the hydrogen is released from the contact member 16 into the handle member 21 via the gas pipe 25 and absorbed by the alloy 23. As a result, the contact surface 17 of the contact member 16 locally refrigerates the article at the portion thereof in contact therewith and freezes the water in the ambient atmosphere to exert an adhering force on the portion of the article The handle member 21 having absorbed the hydrogen evolves 7.5 to 8.0 kcal. of heat per mole of hydrogen.

When the valve is held open for a predetermined period of time, the closed containers 18, 22 of the contact member 16 and the handle member 21 internally reach an equilibrium to discontinue the desorption and absorption of hydrogen If the handle member 21 is heated through a heat conducting surface provided thereon or by an electric heater enclosed therein, the alloy 23 in the handle member 21 desorbs the hydrogen gas, which is then transferred to the contact member 19 via the gas pipe 25 and the valve 26 and absorbed by the alloy 19, whereupon the valve is closed to return the device to the initial state.

Alternatively, an article can be heated by the contact surface 17 of the contact member 16 locally at the portion thereof in contact with the surface 17. In this case, the alloy 19 of the contact member 16 is brought to a hydrogen-desorbed state in advance, with hydrogen held absorbed by the alloy 23 of the handle member 21, and the valve 26 is opened to cause the alloy 23 to desorb the hydrogen and the alloy 19 to absorb the hydrogen.

The contact member 16, when having the improved construction of the first embodiment shown in FIG. 1a or 1b, enables the contact surface 17 to produce an enhanced refrigerating or heating effect concentrically.

With the above embodiment and the modification, the handle member 21 can be provided with a heat-exchange surface as afforded by fins to improve the refrigerating or heat evolving effect of the contact surface 17. Preferably, the contact surface 2, 9 or 17 is shaped in conformity with the shape of the portion of the article to be brought into contact therewith. Especially for the contact surface 2, 9 or 17 to absorb or evolve heat concentrically, the contact surface may be provided by a material having high heat conductivity, with the other portions made of a heat insulating material, ceramics or like material having low heat conductivity. Further to assure the device of ease of manipulation, it is desired that the contact member 1, 8 or 16 and the handle member 21 be so sized and shaped as to be easily handled by the hand and that the piping therebetween be flexible.

If the closed container 22 of the embodiment of FIG. 3 is also provided with a contact surface 9, this contact surface 9 is usable as a heat evolving portion simultaneously while the other contact surface 17 is used as a heat absorbing portion.

Thus, the contact surface 2, 9 or 17 of the contact member 1, 8 or 16 is adapted to locally refrigerate or locally heat articles at the portion thereof in contact therewith and can be utilized, for example, for locally breaking down substances at a cryogenic temperature, cautery, local resolution, etc. Further the contact surface 2 or 17 of the contact member 1 or 16 can be brought into contact with articles, with an adhering force exerted on the site of contact due to the freezing of water on the surface of the article or water in the atmosphere. The contact surface is therefore usable for moving or transporting fragile, readily deformable or soft articles failing to withstand a mechanical holding force, by adhering the article thereto without causing damage to the article. Accordingly, the device is usable also for moving articles which are difficult to handle with the hand or fingers, such as lenses of science and engineering devices, living tissues, etc.

Figure 4A:
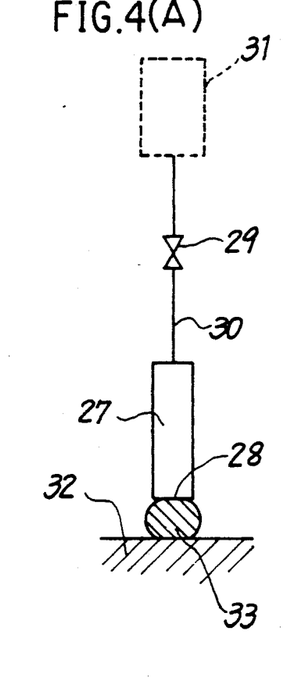
Figure 4B:
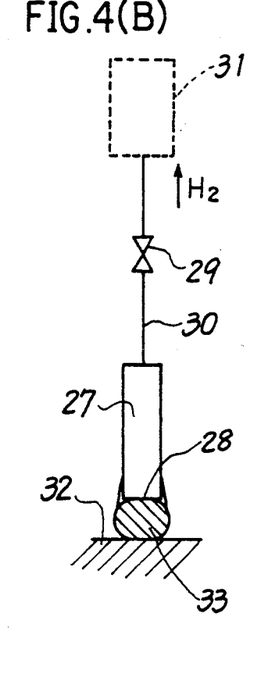
Figure 4C:
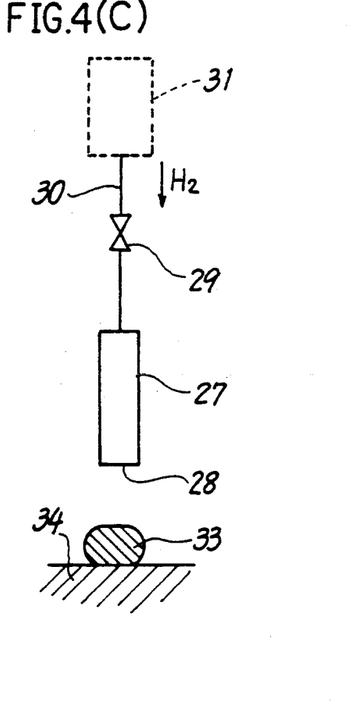

FIG. 4 shows a device of the invention as used for moving or transporting such an article.

With this embodiment, a contact member 27 containing an alloy having hydrogen absorbed therein is provided with a contact surface 28 at its lower end. The contact member 27 communicates with a handle member 31 and a hydrogen source (not shown) via a threeway change-over valve 29 and a pipe 30. The system is movable upward, downward and sidewise in its entirety.

As shown in FIG. 4 (A), the system is lowered toward an article 33 on a table 32 to bring the contact surface into contact with the article 32. As shown in FIG. 4 (B), the contact member 27 is then brought into communication with the handle member 31 by switching the valve 29, whereupon the alloy in the contact member 27 desorbs hydrogen, causing the contact surface 28 to absorb heat and freeze the water in the atmosphere in the vicinity of the contact site or the water on the surface of the article to produce an adhering force on the article 33 due to freezing. Next, the system is raised and moved laterally to a position above another table 34, whereupon the valve 29 is changed over to the hydrogen gas source, causing hydrogen to flow into the contact member 27 for absorption by the hydrogen absorbing alloy. Consequently, the contact surface 28 thaws the frozen water by heating, releasing the article 33 and placing it on the table 34 as shown in FIG. 4 (C). In this way, the article 33 is transferred from the table 32 onto the table 34 while being adhered to the surface 28 free of distortion.

Figure 5:
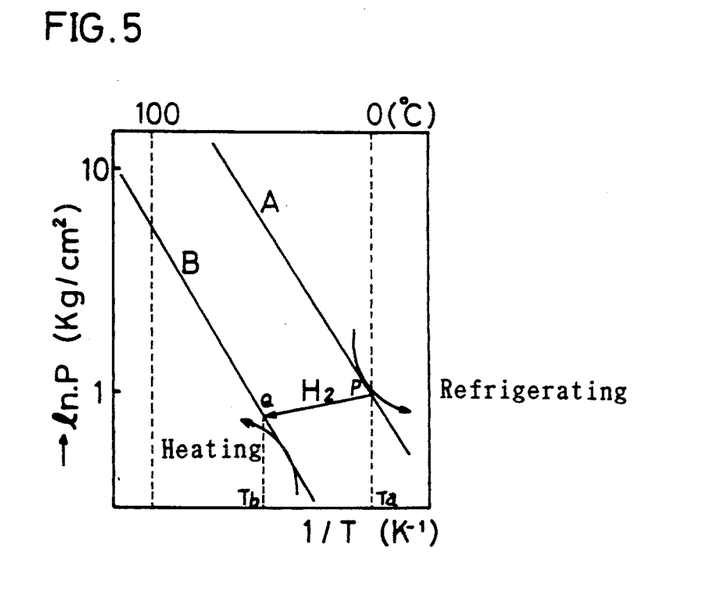
FIG. 5 is a diagram of the temperature characteristics of hydrogen desorption pressure of the third embodiment.

In the case of the embodiment of FIG. 3 wherein the hydrogen absorbing alloy 23 is accommodated in the handle member 21, the factors governing the reduction of temperature of the contact surface 17 are the heat capacity of the alloy 23 and the hydrogen reaction velocity. FIG. 5 shows the temperature characteristics of the hydrogen equilibrium pressure of the hydrogen absorbing alloys 19, 23. When one alloy A has a temperature of Ta and pressure at point P and the other alloy B has a temperature of Tb and pressure at point Q, hydrogen moves from alloy A to alloy B owing to the pressure difference P−Q. When the pressure of one alloy equilibrates with that of the other alloy, the movement discontinues. Alloy A absorbs heat, and alloy B evolves heat. With reference to FIG. 3, suppose the contact member 16 is the hydrogen desorption side, and the handle member 21 is the hydrogen absorption side. If the desorption rate of the contact member 16 is great, the temperature of the contact surface 17 drops markedly.

Figure 6:
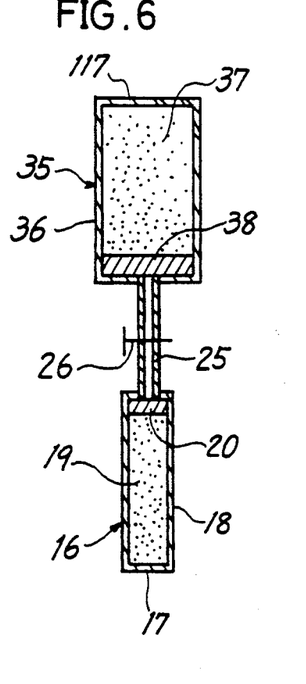
FIG. 6 is a sectional view of a fourth embodiment.
Figure 7:
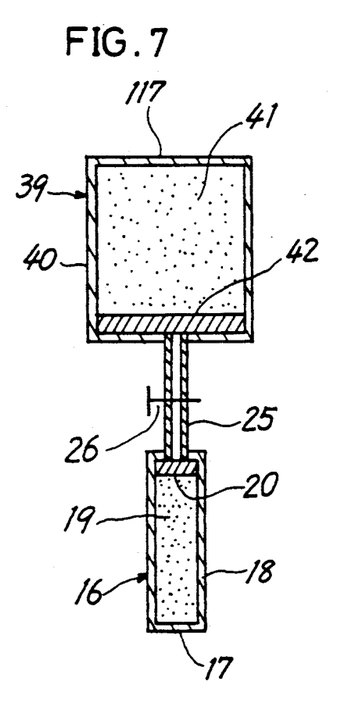
FIG. 7 is a sectional view of a fifth embodiment.

FIGS. 6 and 7 show fourth and fifth embodiments, respectively, each having an altered heat capacity so as to give an increased hydrogen transfer rate. Indicated at 35, 39 are handle members, at 36, 40 are closed containers providing the respective handle members, and at 38, 42 are filters. Hydrogen absorbing alloys 37, 41 packed in the respective closed containers are the same as the alloy 23 accommodated in the handle member 21 of FIG. 3 and are in twice the amount of the alloy 23 (30 g) and three times the amount (45 g), respectively.

Figure 7A:
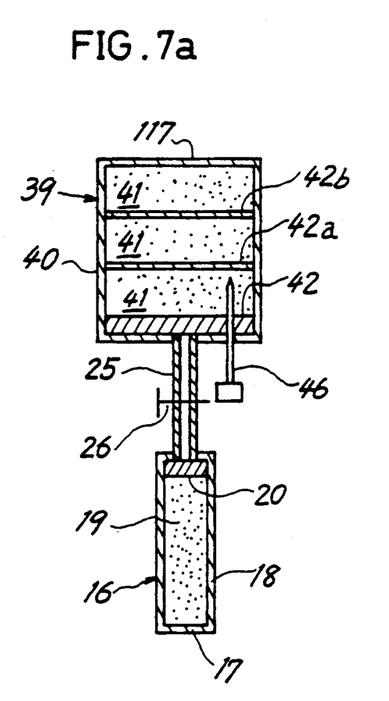
FIG. 7a is a sectional view of an improvement of the fifth embodiment.

Referring to FIG. 7a, the closed container 40 is provided with two partitions 42a, 42b arranged vertically for dividing the container into three sections each packed with the alloy 41, and release means 46 for the partitions 42a, 42b to render the partitions 42a, 42b removable from outside. The single device illustrated in FIG. 7a is serviceable as any one of the devices shown in FIGS. 3, 6 and 7.

Figure 8:
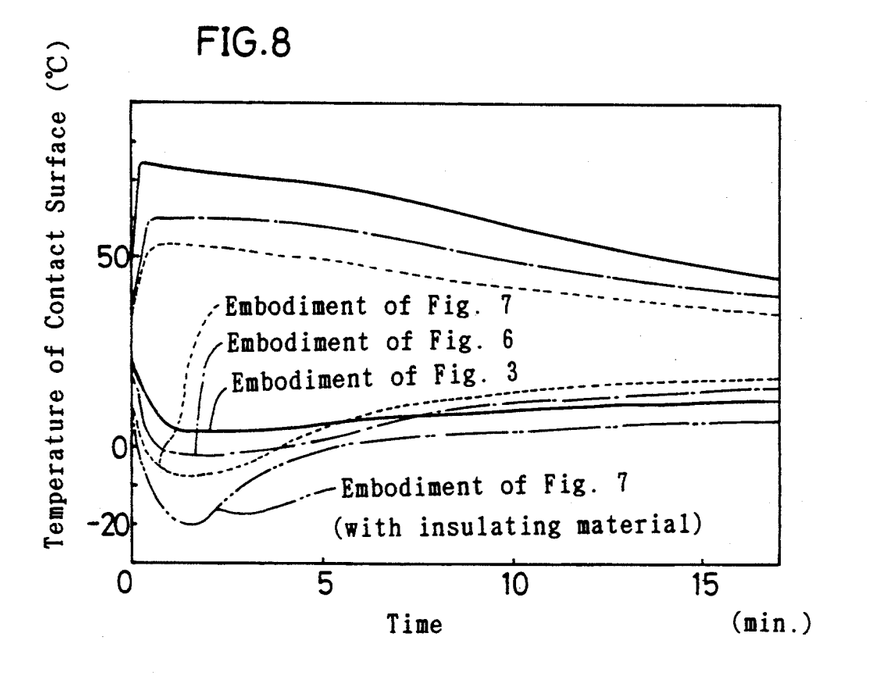
FIG. 8 is a diagram showing the temperature characteristics of the third, fourth and fifth embodiments for comparison.

The lower portion of FIG. 8 is a characteristics diagram showing variations in the temperature of the respective contact surfaces 17 of the embodiments of FIGS. 3, 6 and 7. In the diagram, the solid line corresponds to FIG. 3, the one-dot-and-dash line to FIG. 6, and the broken line to FIG. 7. It is seen that the greater the amount of alloy of the hydrogen absorption side (handle member), the lower can be the temperature available.

The two-dot-and-dash line in the diagram represents the temperature characteristics of the embodiment of FIG. 7 when the side wall of the closed container 18 is covered with a heat insulating material. It is noted that the use of the heat insulating material for separating the heat absorbing portion from the outside air affords a lower temperature than otherwise.

Incidentally, the hydrogen transferred in any of the embodiments represented in FIG. 8 is the hydrogen initially absorbed by the alloy 19 of the contact member, so that these embodiments are the same in the amount of hydrogen and therefore in the quantity of heat absorbed by the contact surface. The embodiments differ only in the lowest temperature of the contact surface 17.

The upper portion of FIG. 8 shows the temperature of the contact surfaces 117 of the handle members 21, 35, 39 obtained by heat evolution. The diagram reveals that the embodiment of FIG. 3 is the highest, followed by the embodiment of FIG. 6 and by the embodiment of FIG. 7 in the descending order of temperature. It is seen that the amount of alloy present on the heat evolution side is preferably smaller when a higher heat evolution temperature is required of the contact surface 117, with lesser importance given to the refrigeration temperature of the contact surface 17 than the heat evolution temperature of the contact surface 117.

With the embodiments of FIGS. 6 and 7, the contact surfaces 17 are usable as heat evolving portions by causing the alloys 37, 41 in the closed containers 36, 40 to absorb hydrogen in advance and returning the hydrogen to the closed container 18.

FIGS. 9 to 17 show applications of the third embodiment of the invention for various uses.

Figures 9, 10:
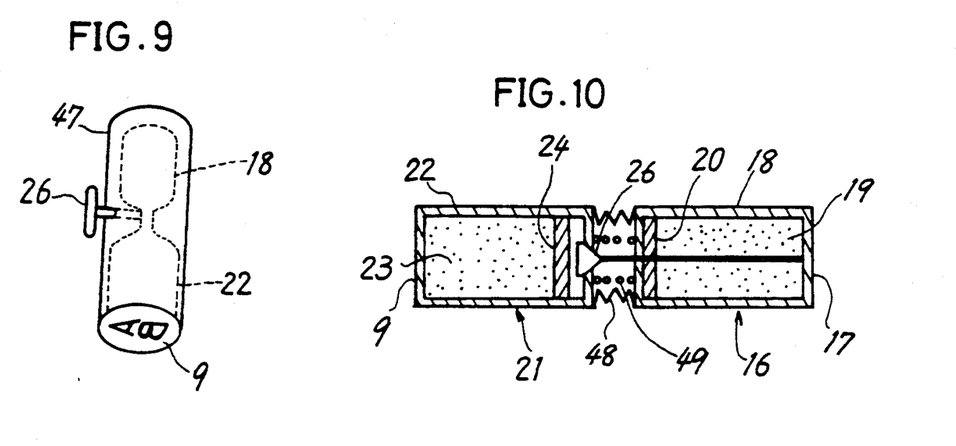
FIGS. 9 to 17 show other embodiments of the invention.

FIG. 9 shows a sealing device comprising a heat evolving closed container 22 having a contact surface 9 as a seal and a heat absorbing closed container 18 which are housed in a casing 47, and a valve provided between the two containers 22, 18. With the contact surface 9 in contact with a sealing wax placed on an important document, the valve 26 is opened and the surface 9 is pressed against the wax, whereupon the contact surface 9 evolves heat to deform the wax for sealing.

FIG. 10 shows a device comprising a contact member 16 and a handle member 21 which are interconnected by bellows 48 and movable toward or away from each other, and a spring 49 for biasing the two members away from each other. A valve 26 is fixed to the contact member 16 and is so disposed as to close an opening of the closed container of the handle member 21 from inside. The valve 26, although holding the container 22 closed usually, is opened by pressing the handle member 21 against an article with the contact surface 17 in contact with the article, whereby the article can be refrigerated.

Conversely, if the contact member 16 is pressed against an article with the contact surface 9 of the handle member 21 in contact with the article, the article can be heated. Accordingly, when the contact surface 9 is in the form of a seal, the device is usable like the sealing device of FIG. 9.

Figure 11:
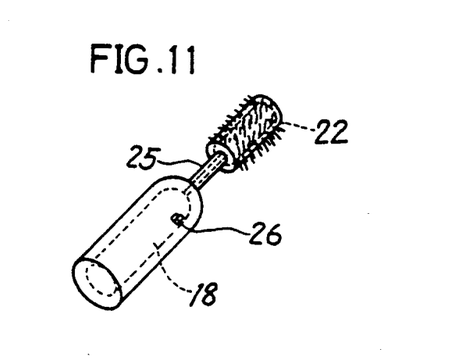

FIG. 11 shows a hot curler comprising a grip portion and a curler portion having closed containers 18, 22, respectively, therein, and a valve 26 provided on the grip portion. When the valve 26 is opened for use, hydrogen gas flows from the grip portion into the curler portion, heating the curler portion to set the hair.

Figure 12:
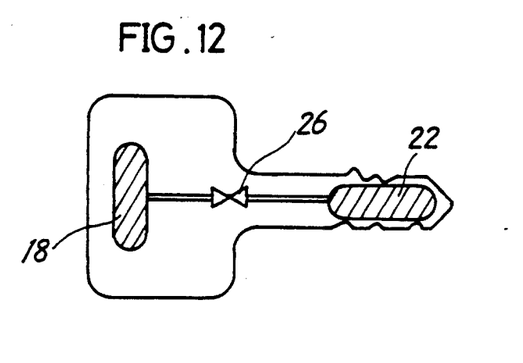

FIG. 12 shows a key for locks installed outdoors or the start locks of motor scooters. The key has incorporated therein a heat evolving closed container 22 at its forward end and a hydrogen gas releasing closed container 18 at its knob portion. Hydrogen gas is allowed to flow into the container 22 in the key end by manipulating a valve 26. When the interior of the key hole is frozen, the valve 26 is opened, causing the key end to evolve heat to thaw the frozen interior of the keyhole for unlocking.

Figure 13:
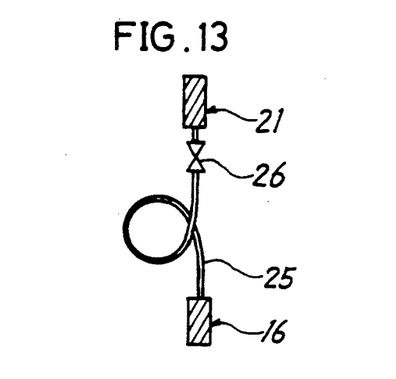

FIG. 13 shows a flexible refrigerator comprising a contact member 16, a handle member 21 and a flexible gas duct 25 interconnecting these members and provided with a valve 26.

The contact member 16 can be inserted into a narrow space of complex configuration to locally heat an inner portion by opening the valve 26 near the hand of the user.

Figure 14:
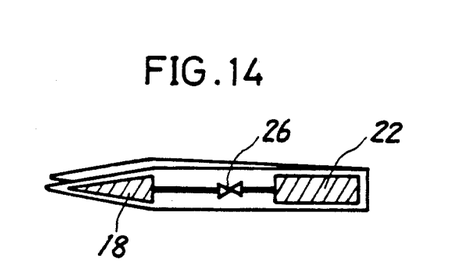

FIG. 14 shows tweezers comprising a hydrogen releasing closed container 18 in a tip, a hydrogen absorbing closed container 22 in the base and, and a valve 26 for holding the two containers in communication. The valve 26 is opened for use to refrigerate the tips, by which an article is nipped in frozen contact therewith without exerting a physical force thereon to move the article.

Figure 15:
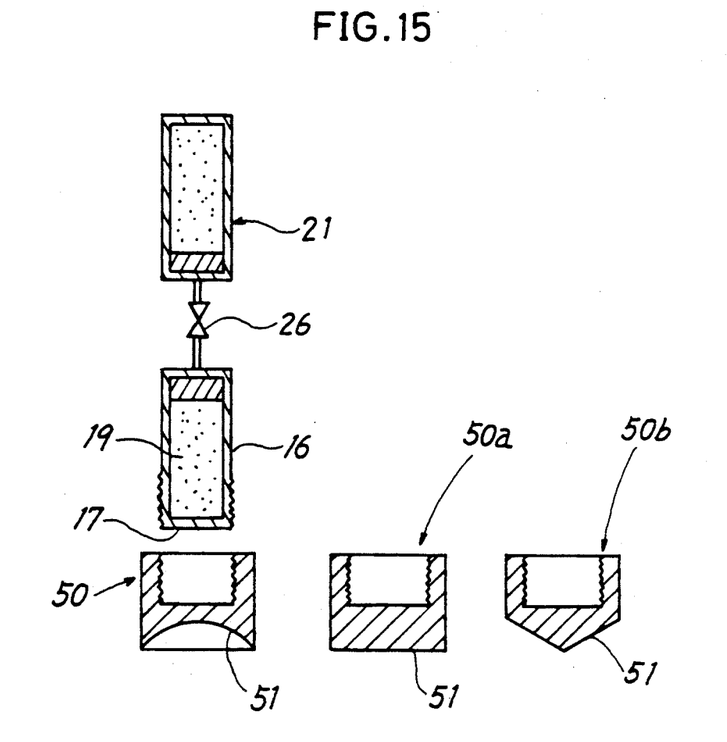

FIG. 15 shows a device for transporting articles similarly in frozen contact therewith. Cassette end pieces 50, 50a, 50b having different curved contact faces 51 shaped in conformity with the surface configurations of articles to be handled can be interchangeably removably attached to the contact surface 17.

Figure 16:
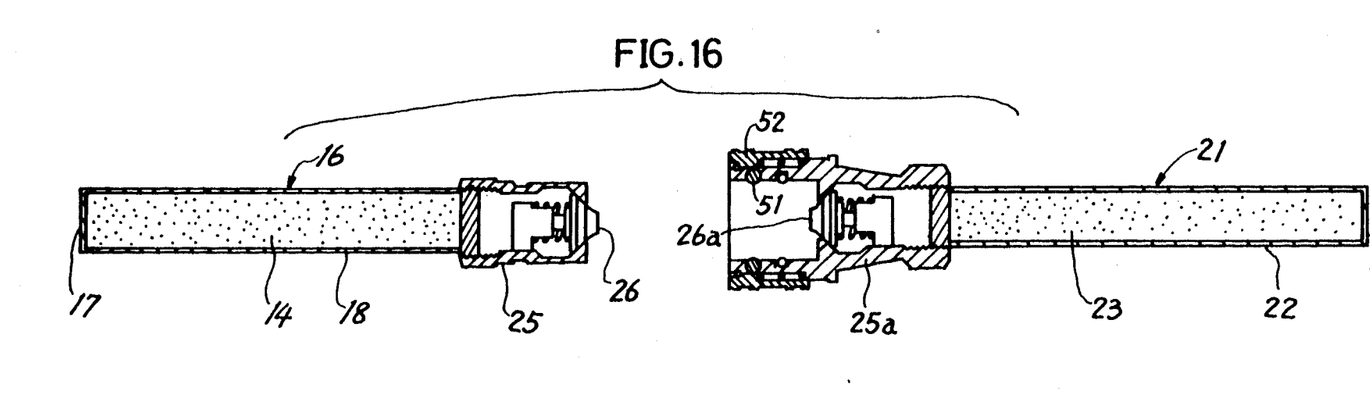

FIG. 16 shows a device comprising a contact member 16 and a handle member 21 removably connectable thereto. One of the closed containers, 18, is provided with a gas pipe 25 closed with a valve 26 and having a connector structure of the spigot type. The other closed container 22 has a gas pipe 25a closed with a valve 26a and having a connector structure of the socket type. The gas pipe 25a of the socket type has a stopper 51 including steel balls, and a slide ring 52. When the gas pipe 25 is inserted into the gas pipe 25a, the two pipes 25, 25a are hermetically connected together and, at the same time, the valves 26, 26a are opened, permitting passage of hydrogen gas. A suitable contact member 16 is selectively usable which has a contact surface 17 shaped in conformity with the shape of the article to be handled.

Figure 17:
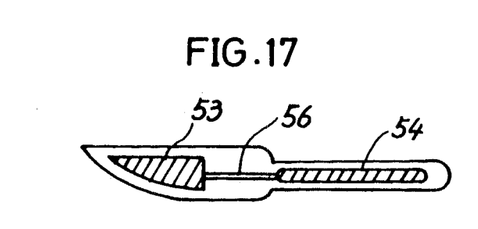

FIG. 17 shows a butter knife wherein closed containers 53, 54, each packed with a hydrogen absorbing alloy, are incorporated respectively in the blade and grip thereof and held in communication with each other by a gas pipe 56 without providing any valve. Usually, the pressures of the two containers are in equilibrium, and no hydrogen gas flows therebetween. When the grip of the butter knife is grasped by the hand, the container 54 of the grip is heated by the body heat, with the result that hydrogen gas flows into the container 53 in the blade on desorption.

Consequently, butter can be cut easily with the heated blade.

The present invention is not limited to the drawings and the foregoing description but can of course be modified or altered by one skilled in the art within the scope of the invention as defined by the appended claims.

What is claimed is:

1. In a hand held portable refrigerator-heater utilizing endothermic and exothermic reactions of a hydrogen absorbing alloy, a refrigerating and/or heating device of the contact type comprising:

a contact member including a closed container, the closed container having a contact surface to be brought into direct contact with an external article and being packed with a hydrogen absorbing alloy, the contact surface outwardly exposed and disposed between the hydrogen absorbing alloy and the external article when the external article is in direct contact with the contact member;

a handle member including a closed container packed with a hydrogen absorbing alloy different in kind from the alloy n the contact member, and the alloy in the handle member which is to absorb hydrogen is greater in amount than the alloy in the contact member which is to desorb hydrogen; a gas pipe means having opposite ends connected to the respective closed containers of the contact member and the handle member in communication with the interior of the containers, wherein the gas pipe means allows hydrogen to interchangeably pass between the hydrogen absorbing alloys of the contact member an the handle member; and a valve disposed in the contact member-gas pipe-handle member channel, one of the contact member and the handle member being higher in hydrogen equilibrium pressure than the other when serving as a hydrogen desorption side.

2. A device as defined in claim 1 wherein the closed container of the handle member has a contact surface to be brought into direct contact with an external article, and when the contact surface of the contact member absorbs heat, the contact surface of the handle member evolves heat.

* * * * *